(12) United States Patent
Mawby et al.

(10) Patent No.: US 9,645,052 B2
(45) Date of Patent: May 9, 2017

(54) TIRE UNIFORMITY THROUGH IDENTIFICATION OF PROCESS HARMONICS USING RE-INDEXED PARTIAL UNIFORMITY WAVEFORMS

(75) Inventors: William David Mawby, Greenville, SC (US); Jimmy Jeter, Greenville, SC (US); Jonathan Sauls, Greenville, SC (US); James Michael Traylor, Greenville, SC (US)

(73) Assignees: MICHELIN RECHERCHE et TECHNIQUE S.A., Granges-Paccot (CH); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 14/344,945

(22) PCT Filed: Sep. 16, 2011

(86) PCT No.: PCT/US2011/051865
§ 371 (c)(1),
(2), (4) Date: Mar. 14, 2014

(87) PCT Pub. No.: WO2013/039505
PCT Pub. Date: Mar. 21, 2013

(65) Prior Publication Data
US 2014/0338437 A1 Nov. 20, 2014

(51) Int. Cl.
*B29D 30/06* (2006.01)
*G01M 17/02* (2006.01)
(Continued)

(52) U.S. Cl.
CPC ......... *G01M 17/02* (2013.01); *B29D 30/0061* (2013.01); *B29D 30/0633* (2013.01);
(Continued)

(58) Field of Classification Search
CPC ................ B29D 30/0061; B29D 30/08; B29D 2030/082; B29D 2030/0066; G01M 17/02
See application file for complete search history.

(56) References Cited

U.S. PATENT DOCUMENTS 5,882,452 A * 3/1999 Sakamoto ............. B29D 30/26
156/111
5,938,869 A * 8/1999 Kaido et al. .................. 152/510
(Continued)

FOREIGN PATENT DOCUMENTS

| WO | WO2005051640 | 6/2005 | |
| WO | WO 2010/126516 | 11/2010 | |
| WO | WO 2012/002949 | * 1/2012 | ............ G06F 19/00 |

OTHER PUBLICATIONS

GSP9700 Series Vibration Control System Hunter Engineering Company, 2004.*

*Primary Examiner* — Martin Rogers
(74) *Attorney, Agent, or Firm* — Dority & Manning, P.A.

(57) ABSTRACT

Systems and methods for improving tire uniformity include identifying at least one candidate process harmonic and corresponding period. A set of uniformity waveforms is then collected for each test tire in a set of one or more test tires. To provide better data for analysis, the collection of waveforms may include multiple waveforms including measurements obtained before and/or after cure, in clockwise and/or counterclockwise rotational directions, and while the tire is loaded and/or unloaded. The uniformity waveforms may be re-indexed to the physical order of the at least one candidate process harmonic, and selected data points within the waveforms may optionally be deleted around a joint effect or other non-sinusoidal effect. The re-indexed, optionally partial, waveforms may then be analyzed to determine magnitude and azimuth estimates for the candidate process harmonics. Aspects of tire manufacture may then be modified
(Continued)

in a variety of different ways to account for the estimated process harmonics.

2 Claims, 8 Drawing Sheets

(51) Int. Cl.
*B29D 30/00* (2006.01)
*G01N 29/44* (2006.01)

(52) U.S. Cl.
CPC ... *G01N 29/449* (2013.01); *B29D 2030/0066* (2013.01); *B29D 2030/0634* (2013.01)

(56) References Cited

U.S. PATENT DOCUMENTS

| | | | |
|---|---|---|---|
| 6,386,945 B1 * | 5/2002 | Fahringer | B24B 5/366 451/10 |
| 6,514,441 B1 * | 2/2003 | Tanaka et al. | 264/40.1 |
| 6,856,929 B1 * | 2/2005 | Mawby | B29D 30/0662 702/84 |
| 7,012,701 B2 * | 3/2006 | Hassler | G01B 11/25 356/601 |
| 7,069,135 B2 | 6/2006 | Bertrand | |
| 7,213,451 B2 | 5/2007 | Zhu | |
| 7,240,542 B2 | 7/2007 | Gustafsson | |
| 7,558,618 B1 * | 7/2009 | Williams | A61B 5/0059 600/407 |
| 7,790,075 B2 | 9/2010 | Hair, Jr. | |
| 2004/0238986 A1 * | 12/2004 | Kobayashi | B29D 30/0662 264/40.1 |
| 2006/0062076 A1 * | 3/2006 | Shimada | B29C 47/0019 366/88 |
| 2006/0137802 A1 | 6/2006 | Flament et al. | |
| 2007/0137763 A1 * | 6/2007 | Burg | B29D 30/0061 156/123 |
| 2007/0172533 A1 * | 7/2007 | Pinchot | 425/142 |
| 2008/0282799 A1 * | 11/2008 | Douglas | G01M 1/16 73/460 |
| 2011/0114251 A1 | 5/2011 | Mawby et al. | |

* cited by examiner

TIRE UNIFORMITY THROUGH IDENTIFICATION OF PROCESS HARMONICS USING RE-INDEXED PARTIAL UNIFORMITY WAVEFORMS

FIELD OF THE INVENTION

The invention relates to tire uniformity, and more specifically to a system and method for improving tire uniformity by reducing the impact of process harmonics that have been estimated from properly indexed and joint effect mitigated analysis of multiple uniformity waveforms.

BACKGROUND OF THE INVENTION

Tire non-uniformity relates to the symmetry (or lack of symmetry) relative to the tire's axis of rotation in mass, geometric or stiffness characteristics. Conventional tire building methods unfortunately have many opportunities for producing non-uniformities in tires. During rotation of the tires, non-uniformities present in the tire structure produce periodically-varying forces at the wheel axis. Tire non-uniformities are important when these force variations are transmitted as noticeable vibrations to the vehicle and vehicle occupants. These forces are transmitted through the suspension of the vehicle and may be felt in the seats and steering wheel of the vehicle or transmitted as noise in the passenger compartment. The amount of vibration transmitted to the vehicle occupants has been categorized as the "ride comfort" or "comfort" of the tires.

Many different factors can contribute to the presence of non-uniformities in tires, even when the tires are built under seemingly identical process conditions. Examples of such factors include the location of product start points and/or joint overlap locations for one or more of the many complex tire building products and/or steps. Exemplary products include the casing textile plies, the belt plies, bead rings, the inner liner, the tread and other rubber layers. Steps involving these and other products include the application of such products to a form or drum, placing the resulting green structure in a mold or press and subjecting the structure to heat and pressure to shape and cure the rubber products and bond the materials into an integrated cured tire unit. Manufacturing variations associated with the above factors can manifest in the form of harmonic contributions to a tire's uniformity.

Although some methods and systems have been developed relating to harmonic component estimation of tire uniformity, additional improvements in accuracy of such estimation are desired. No known design has yet emerged that generally encompasses all of the desired characteristics as hereafter presented in accordance with the disclosed technology.

SUMMARY OF THE INVENTION

In view of the recognized features encountered in the prior art and addressed by the present subject matter, an improved system and method has been provided to improve uniformity in tires. Such method generally involves steps to estimate a candidate process harmonic magnitude and azimuth and then to use these estimates to directly improve the uniformity of each individual tire by suppressing the candidate process harmonic or by opposing it to other process harmonics or tire harmonics in an automatic maintainable system.

The subject technology involves measuring a given uniformity parameter for each tire in a set of test tires. For example, such uniformity parameters may selectively include one or more of radial run out (RRO), lateral run out (LRO), balance, mass variance, radial force variation (RFV), lateral force variation (LFV) and tangential force variation (TFV). In some examples, it is preferred to obtain a collection of multiple uniformity waveforms, including both a loaded tire measurement (e.g., RFV, LFV or TFV) and an unloaded tire measurement (e.g., RRO or LRO). In other examples, the multiple uniformity waveforms include a waveform measured before the tire is cured and a waveform measured after the tire is cured. In still further examples, the multiple uniformity waveforms include a measurement obtained while rotating a test tire in the clockwise direction and a measurement obtained while rotating a test tire in the counterclockwise direction. The multiple uniformity waveforms add more data points for analysis and also help to identify and resolve any discrepancies that arise due to discrete data point analysis.

In some examples, the measured values correspond to a composite waveform comprised of a plurality of data points measured circumferentially around a tire, where the composite waveform contains tire harmonics as well as at least one candidate process harmonic. Rectangular coordinate coefficients are electronically constructed for the at least one candidate process harmonic, after which point the rectangular coordinates corresponding to each process harmonic are solved for (e.g., by using regression-based analysis) to ultimately produce estimates of each process harmonic magnitude and azimuth. The regression-based analysis may be conducted using the raw data of the composite uniformity waveform, or it may be conducted using data that has been conditioned in accordance with one or more improvement techniques disclosed herein. In a first example, a collected set of uniformity waveforms is re-indexed to the physical order of a selected process harmonic. When different process harmonics are analyzed, the data can be re-indexed multiple times to accommodate the physical order of each respective process harmonic. In addition, selected data points optionally may be deleted from selected uniformity waveforms to remove data skew caused by joint effects or other non-sinusoidal process effects.

In additional exemplary embodiments, once the magnitude and azimuth of process harmonics is determined, the process harmonics can be separated from the tire harmonics, and new tires can be built to improve uniformity based on such knowledge. For example, the relative location of the at least one candidate process harmonic can be changed in subsequent tires in order to reduce the combined average magnitude of the tire harmonics and the at least one candidate process harmonic.

In addition to various methods, it is to be understood that the present subject matter equally relates to associated systems, including various hardware and/or software components that may be provided in a tire manufacturing and measurement system in order to implement selected features as disclosed herein.

It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
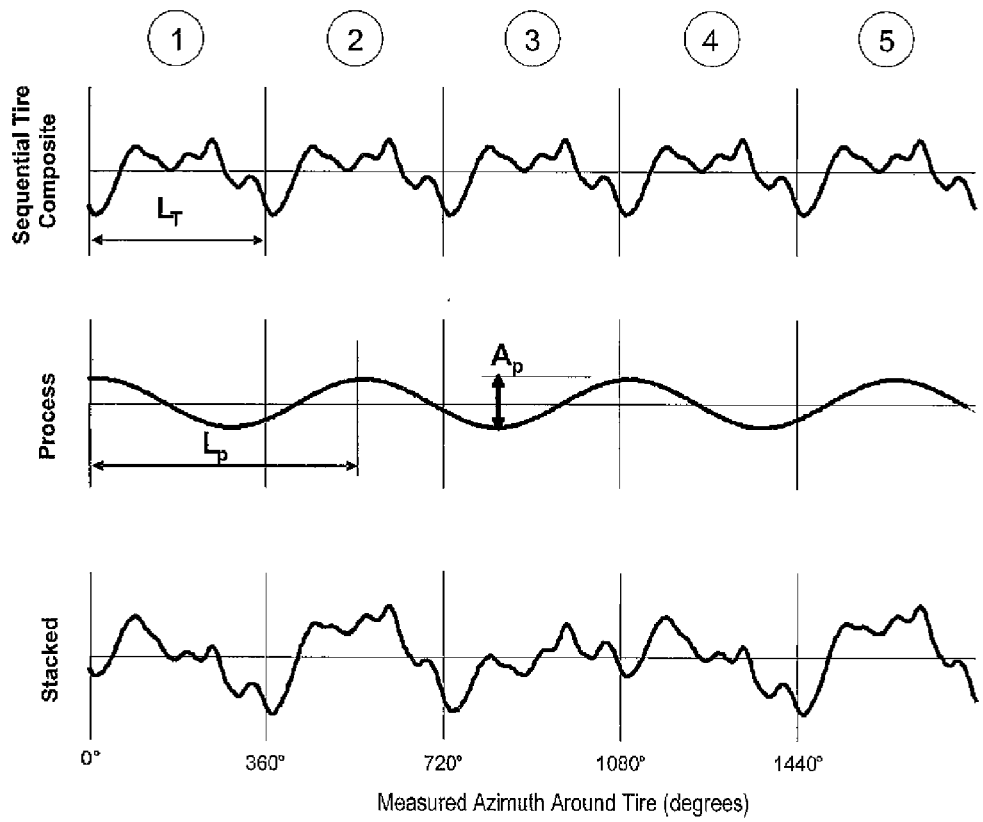
FIG. 1 provides a graphical representation of 5 "stacked," or concatenated, sequential uniformity waveforms, decomposed into sequential tire composite waveforms and a process harmonic waveform having magnitude $A_p$ and process harmonic number p.

Repeat use of reference characters throughout the present specification and appended drawings is intended to represent same or analogous features, elements or steps of the present invention.

DETAILED DESCRIPTION OF THE PREFERRED EMBODIMENTS

As discussed above, the present subject matter is particularly concerned with a system and method for improving tire uniformity by automatically opposing process harmonics to other tire or process harmonics on a tire-by-tire basis within the natural manufacturing process, where the process harmonics have been estimated from properly indexed and joint effect mitigated uniformity waveforms.

In analyzing tire uniformity, a variety of different uniformity parameters may be measured for a set of one or more test tires. The obtained measurements generally correspond to a composite waveform representative of tire uniformity, which can be decomposed into many respective harmonic contributions. The test tires, even when manufactured under like conditions, are subject to variation in uniformity due to cyclic manufacturing variations that occur in two primary ways. In a first case, the periods of the manufacturing variation coincide with the tire circumference. These are referred to herein as "tire harmonics" because they are associated with the tire circumference. Typical tire harmonics include tread joint width, the out-of-roundness of the building drums, and press effects. In a second case, the periods of the manufacturing variations do not coincide with the tire circumference. Although these manufacturing variations are cyclic, their periods are not integer divisors of the tire circumference. These are referred to herein as "process harmonics" because they are related to process elements rather than tire circumferences. Typical process harmonics include cyclic variation tread thickness caused by the extruder control system or rollers which may deform the shape of softer products.

In order to use the knowledge of process harmonics to effect uniformity improvements, it is necessary to estimate their periods, magnitudes, and azimuths. Given knowledge of these characteristics of the process harmonics, one can then oppose the process harmonics against tire harmonics or other process harmonics or within themselves to produce tires that have better uniformity parameter values in both magnitude and dispersion. For example, the position of the process harmonic high point (say tread extruder thickness effect) may be tracked relative to its entry point into the press and automatic real-time adjustments can be made to oppose this known process high point to the high point of the press (a tire harmonic) so the resultant tire uniformity after curing can have a lower magnitude more consistently. One may also offset other harmonics, such as the relative location of the tire carcass from a first tire building stage and the tread/belts from a second tire building stage in order to achieve a similar uniformity improvement. In addition, it is possible to change the period of the process harmonic to better match the set of identified tire harmonics in the tire. For example, the tread extruder could be slowed or accelerated to introduce the process harmonic at a different location within a tire.

Since adjustments will be different for each tire, this opposition process can be applied tire-by-tire automatically in the production process. Such improved tires could improve customer performance satisfaction and reduce manufacturing costs. Due to the importance of reliably estimating the process harmonics, improved techniques for pre-treatment of the uniformity waveforms is disclosed herein.

Referring now to FIG. 1, a graphical representation shows how a process harmonic can add to existing tire harmonics to cause uniformity variation across multiple consecutively manufactured tires. In FIG. 1, the top graph labeled "Sequential Tire Composite" represents five different uniformity waveforms that are obtained for five respective test tires. Those five waveforms are then stacked sequentially one after the other to obtain a concatenated waveform as shown in the top graph of FIG. 1. The uniformity waveform for each tire is composed of a number of different tire harmonics, each of which fit an integer number of times within the period defined by the tire circumference, namely $L_T$. If a process harmonic represented by the second graph is added to the tire harmonics of the first graph, then a stacked waveform represented as shown in the third graph results. The process harmonic represented in the second graph can be modeled as a periodic function $$f_p(\theta) = \frac{A_p}{2} \cos p(\theta - \theta_p),$$

where p is the harmonic number associated with the process effect, whose process harmonic number p is defined as $L_T/L_P$.

Figure 2:
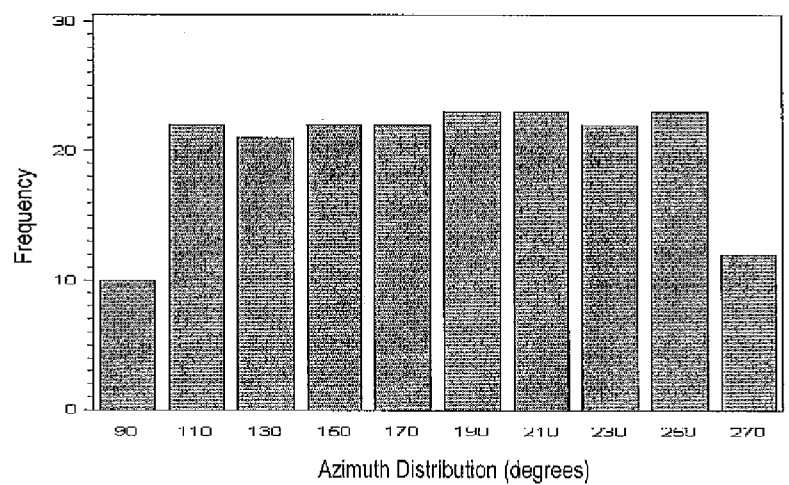
FIG. 2 provides a histogram graph of exemplary azimuth values for a particular process harmonic across multiple test tires.

Referring still to FIG. 1, it is evident that the addition of a process harmonic to a uniformity waveform can cause the maximum values within the uniformity waveform (or particular harmonic components thereof, e.g., the first harmonic of a radial force variation measurement) to vary from tire to tire even if all tire harmonics remain constant. The distribution from tire to tire of the azimuths corresponding to maximum values within a uniformity waveform will depend on the relationship between the period of the process harmonic ($L_P$) to the period of the first tire harmonic ($L_T$). For example, consider a constant tire component with amplitude 1 kg at 0 degrees in combination and a single process harmonic having a harmonic number of p=1.25 (such as from a tooling component such as a tread cooling drum) with amplitude 0.5 kg in synchrony with one another for the first tire in a production sequence. The uniformity magnitude of the first tire will be 1.5 kgs at an azimuth of 0 degrees but the second tire will have a uniformity magnitude of 1.12 kgs at an azimuth of 27 degrees. The third tire will have a uniformity magnitude of 0.5 kgs at an azimuth of 0 degrees. Then tire 4 will have a uniformity magnitude of 1.12 kgs at an azimuth of −27 degrees. Finally tire 5 will repeat tire 1, tire 6 will repeat tire 2, and so on with the values cycling through these 4 possibilities. So the histogram of azimuths would only have three values: 0, 27 and −27 degrees. However, a different single process harmonic having a process harmonic number of p=1.1123 (such as might come from a product that is stretched over the building drum) will have many more azimuth values corresponding to the maximum value within a uniformity waveform and the histogram of these azimuth values will resemble that of a uniform distribution, such as shown in the exemplary histogram of FIG. 2.

The movement of the process harmonic azimuth and the resultant movement in the observed total harmonic azimuth can cause challenges for the use of the process harmonics in process improvement. The standard signature analysis approach for tire uniformity depends on the study of effects (such as building drums) that are aligned with tire circumferences, i.e., tire harmonics. A process harmonic does not naturally fit into the standard signature analysis approach because a process effect will, in general, cause an azimuth shift in every tire and will simultaneously affect multiple tire harmonics. This means that process harmonics will appear as dispersion and hence will not be identified in the standard signature analysis approach. Because of this negative influence the identification of process harmonics can correct some of the errors made in applying standard signature analysis naively. When dealing with process harmonics, it can be especially important to distinguish between the physical source and its impact on the harmonics. This means that the task of identifying process harmonics should be done with as much accuracy and precision as possible.

Figure 3:
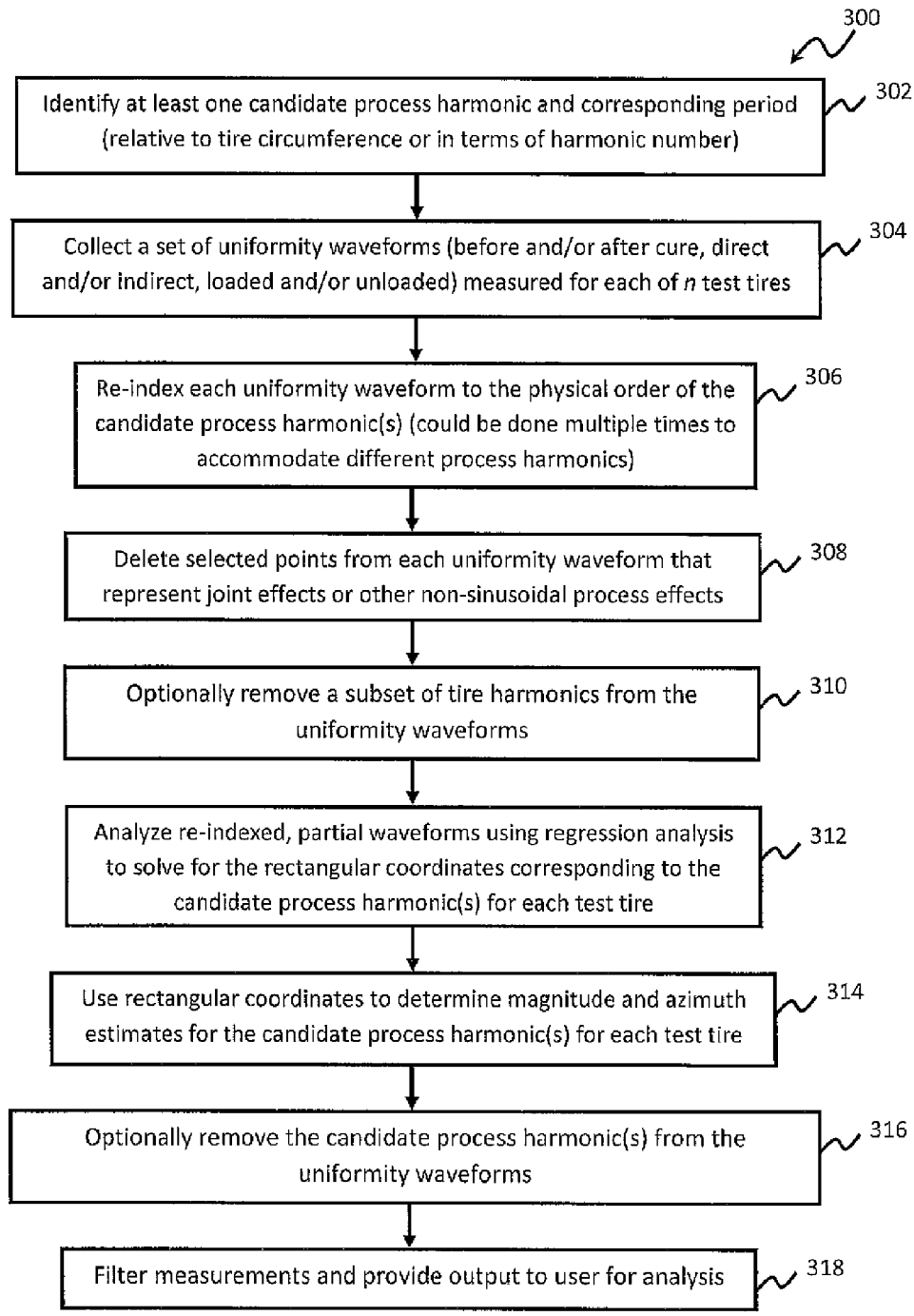
FIG. 3 provides a flow chart of exemplary steps in an improved method of identifying process harmonics in a uniformity waveform in accordance with the present technology.

Referring now to FIG. 3, a method 300 of identifying process harmonics in a uniformity waveform is presented, and may include exemplary steps 302-312, respectively. In step 302, at least one manufacturing variation giving rise to a candidate process harmonic is identified as well as a corresponding period for the candidate process harmonic(s). In some embodiments, the period of each process harmonic may be defined relative to the dimensions of the tire (e.g., tire circumference, radius, diameter, discrete number of measured data points around the tire or the like). The process harmonic can also be a harmonic number which is simply the tire circumference divided by the process harmonic period. For example, a process harmonic having a period of 1.0 meters on a tire having a 1.25 meter circumference would have a harmonic number of 1.0/1.25=0.8

Referring still to FIG. 3, step 304 involves collecting a set of one or more uniformity waveforms that are measured for each of n test tires. Each uniformity waveform may correspond to a measured uniformity parameter corresponding to, for example, such uniformity parameters as radial run out (RRO), lateral run out (LRO), mass variance, balance, radial force variation (RFV), lateral force variation (LFV) and tangential force variation (TFV). Examples that discuss selected ones of the above parameters are presented herein for illustrative purposes only and should not be unnecessarily limiting to the present invention. The measured parameter often corresponds to a waveform constructed from a number of data points measured in equally spaced points during one rotation of a tire (e.g., 128, 256, 512 or other number of data points per tire revolution).

Consider a measured uniformity parameter (U) that is obtained at a plurality of equally spaced data points N around a tire such that measurements are obtained at respective data points $U_n$, for n=1, 2, . . . , N. It should be appreciated that the actual $U_n$ values may be conditioned in accordance with a variety of known techniques. For example, the $U_n$ values may be obtained at more than just a single rotation of a tire by averaging the obtained values at each data point during multiple rotations of the tire. In another example, the $U_n$ values may be conditioned by subtracting out the average magnitude value of the measured uniformity parameter across all respective data points such that the composite data waveform is centered around an origin of reference.

Referring still to FIG. 3, aspects of steps 304-308, respectively, represent at least three different ways to improve the identification and estimation of process harmonics within a uniformity waveform, one or more of which selectively may be implemented in various embodiments of the disclosed technology. These methods are applied in order to produce reliable information on which to base the automatic uniformity improvement system. It is especially important to estimate these process harmonic contributions correctly because on-line identification is not usually performed and the estimates are used to direct process adjustments over a long time period. The three improvements generally include re-indexing uniformity waveforms as indicated in step 306, obtaining partial waveforms be deleting selected points as indicated in step 308, and obtaining multiple different types of uniformity waveforms as represented in step 304.

Referring to step 306 of FIG. 3, one exemplary improvement generally involves a step of re-indexing obtained uniformity waveforms so that the break between the waveforms for consecutive tires matches the physical order of a candidate process harmonic. In general, the term "re-indexing" refers to a reordering of consecutively measured data points around a tire. This improvement is important to account for the fact that the continuously generated process harmonic signal (e.g., the uniformity contribution resulting from a tread thickness cycle caused by a material extruder in forming a green tire) is made discontinuous when it is periodically cut to form a layer or portion for each sequentially manufactured tire and then is joined end-to-end to make the product joint.

The effects of product joints or other manufacturing variations within a tire vary with consecutively manufactured tires. However, the relative order in which these variations occur within a tire may not match the order in which uniformity waveforms are measured on consecutively manufactured tires. Uniformity waveforms are usually measured relative to a marker, such as a barcode, or other visible identifier on a tire which defines an initial tire measurement point. All other uniformity data points measured around a tire circumference are indexed relative to this initial marker defining a zero point. As such, the obtained waveform needs to be re-indexed to the physical order of a process harmonic's manufacturing variation such that the beginning and end of a uniformity waveform match to the beginning and end of the physical introduction of a particular process harmonic within the uniformity waveform. For different selected process harmonics, this re-indexing could be done multiple times, once each to correspond to the physical order of each candidate process harmonic's manufacturing variation.

Figures 5A, 5B:
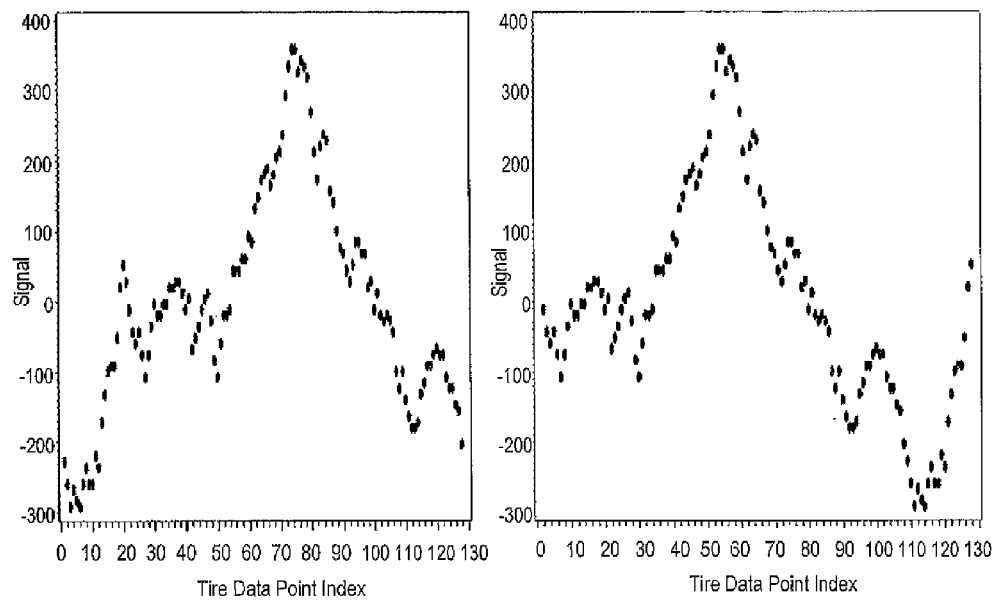
FIGS. 5A and 5B provide graphical illustrations of an original uniformity measurement and an adjusted uniformity measurement for a single tire after applying a re-indexing step in accordance with the disclosed technology.
Figures 6A, 6B:
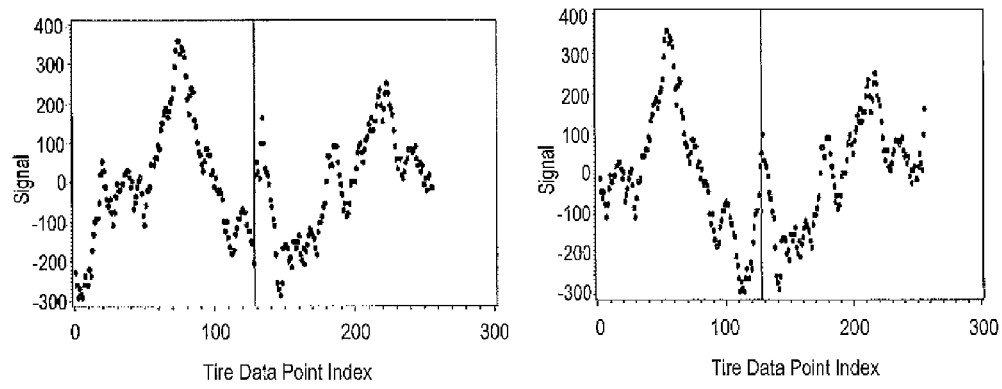
FIGS. 6A and 6B provide graphical illustrations of an original uniformity measurement and an adjusted uniformity measurement for two consecutive tires after applying a re-indexing step in accordance with the disclosed technology.
Figure 7:
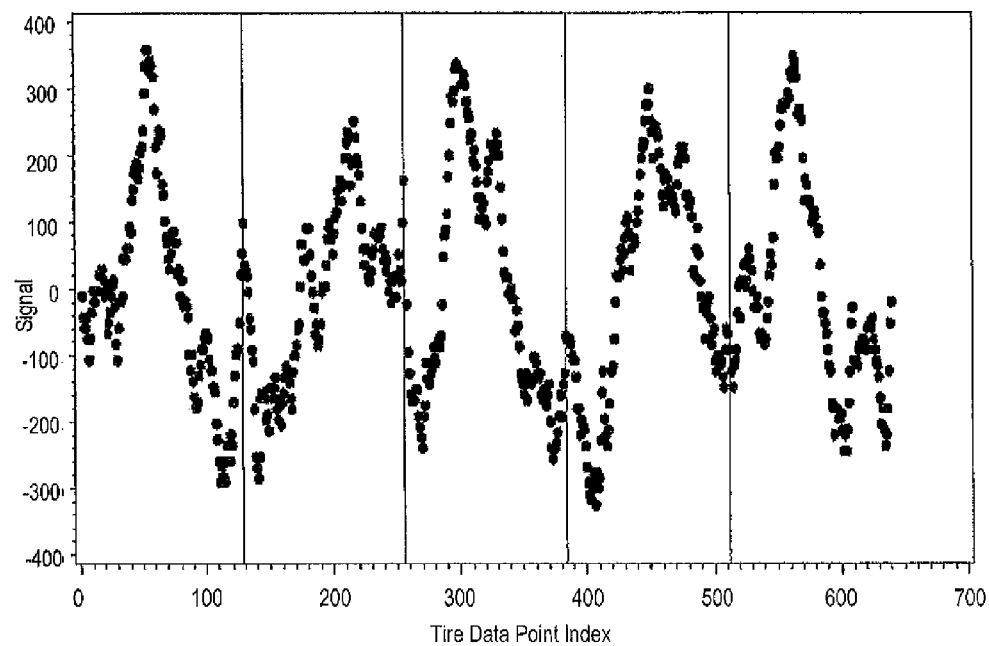
FIG. 7 provides a graphical illustration of an adjusted uniformity measurement for five consecutive tires after applying a re-indexing step in accordance with the disclosed technology.

Specific examples related to the re-indexing of a uniformity waveform are presented in FIGS. 5A, 5B, 6A, 6B and 7. FIG. 5A shows an original uniformity waveform obtained for a given tire, more particularly including a radial run out plot indexed at 128 points around the circumference of a tire. Assuming that a product joint introducing a process harmonic of interest is located at point 20 within the waveform of FIG. 5A, the waveform could be re-indexed to form the adjusted waveform of FIG. 5B by making point 20 the first point in the waveform. FIGS. 6A and 6B show a similar relative change between original uniformity waveforms of FIG. 6A to the adjusted waveforms of FIG. 6B. In the example of FIGS. 6A and 6B, two consecutive tires are re-indexed in a similar way as represented in FIGS. 5A and 5B in order to show the potential impact of this approach on the continuity of the analyzed waveforms, A series of waveforms from five consecutive tires re-indexed beginning at the center of a joint is shown in FIG. 7.

Figure 8:
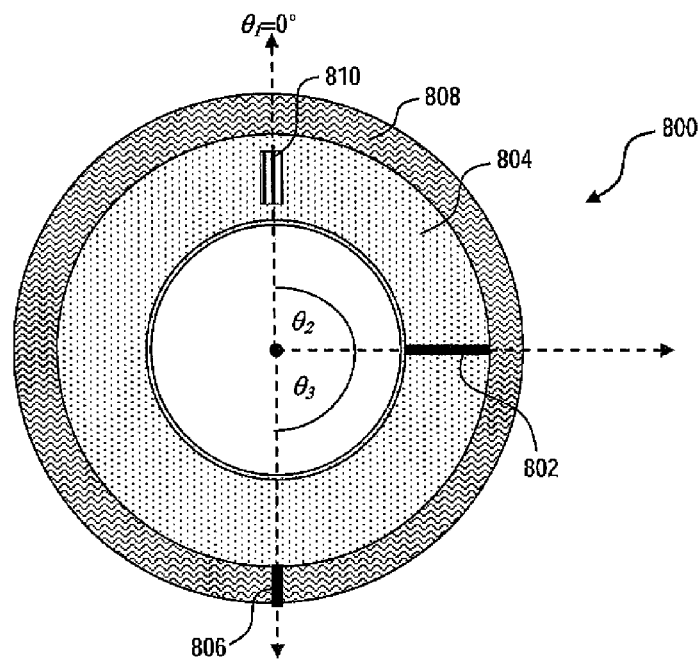
FIG. 8 provides a schematic representation of the relative location of multiple joint effects relative to a known marker on a tire, such as a barcode.

Another example of re-indexing is provided relative to FIG. 8. Consider a tire 800 that includes a first joint 802 resulting from the formation of a first tire layer 804 and a second joint 806 resulting from the formation of a second tire layer 808. The relative locations of the first joint 802 and second joint 806 (i.e., $\theta_2$ and $\theta_3$, respectively) are usually known or can be determined. A bar code 810 is an example of a visual marker on tire 800 that is used to signal the measuring start and end of a uniformity waveform around the tire circumference. The relative location of the bar code 810 is depicted as $\theta_1=0°$.

Referring still to FIG. 8, consider that a process harmonic due to the cycling of tread thickness from an extruder used in the construction of the stacked waveforms from three consecutively manufactured tires might have an index order of points 1 to 128 for tire 1, 129-256 for tire 2, and 257-384 for tire 3. This indexing represents the production order coming from the extruder. However, the joint for this product might be located 90 degrees or 32 points (of a 128 point waveform) away from the barcode. That is, the waveforms, when stacked according to measurement order, will not match the production order. Specifically, the measured order will be 33-128, 1-32, 161-256, 129-160, 289-384, 257-288, which prevents a close match between the endpoints of stacked waveforms. This can cause error in the estimation of the process harmonics in stacked or singlet waveforms.

A re-indexing step 306 can be applied to the obtained uniformity waveform to match the correct physical ordering of the process harmonic to overcome this difficulty. In some embodiments, this re-indexing simply means using the process order as opposed to the measured order before using a singlet-based analysis. In other embodiments, re-indexing means changing the order of the points to that of the process order before using a stacked method such as Fourier analysis or regression. Notice that since different products have different joint locations it might be necessary to reorder in multiple ways if one is studying more than one candidate process harmonic. For example, the tire product 804 might have the joint location 802 as described above, but the second joint 806 from product 808 might be at 180 degrees (64 points) from the measurement zero point. Then one would use the first joint ordering of 33-128, 1-32, 161-256, 129-160, 289-384, 257-288 and the second joint ordering of 65-128, 1-64, 193-256, 129-192, 321-384, 257-320 in the same regression. Other joints could be handled by including their proper ordering into the analysis in a similar way.

Figure 9:
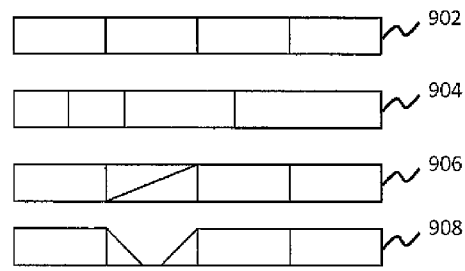
FIG. 9 provides a schematic depiction of the four different potential joint effects for causing data skew in accordance with some tire instances.

Referring again to step 308 of FIG. 3, a second exemplary improvement generally involves deleting selected points within an obtained uniformity waveform that represent joint effects or other non-sinusoidal process effects. This improvement helps to remedy the situation that arises when the physical construction of a joint stretches or compresses the material in the neighborhood of the joint, as depicted in FIG. 9. The use of joint presses can also alter the effect in the neighborhood of the joint. In FIG. 9, portion 902 represents regular spacing at measurement points around a joint location, while portion 904 represents stretched spacing that may occur around a joint location. There can also be an overlap of product at the joint as represented by portion 906, or even an opening at the joint where there is no product at all, as represented by portion 908. In any of these cases, the regular spacing between measurement points can be distorted from the true spacing of the underlying process harmonic. This too can impact the process harmonic estimation process.

In order to correct for measurement issues arising because of material deformities around a joint, a select number of points around the joint location can be deleted from the uniformity waveform. The number of points to be deleted can come from knowledge of the type of signal being measured (e.g., a loaded or unloaded tire signal such as run-out or force variation) and one's knowledge of the historical joint effect. As a general example, one might delete a number of points within a range from 2-10 on either side of the joint. In one particular example, 5 points are deleted on either side of the joint, leaving 128-10=118 points on which to base the estimation procedure when 128 data points are measured around a tire.

Referring again to step 304 of FIG. 3, a third exemplary improvement generally involves analyzing a set of uniformity waveforms, wherein the uniformity waveforms include multiple waveforms obtained in one or more of a variety of fashions—e.g., before and/or after cure, direct and/or indirect (i.e., clockwise or counterclockwise rotation) and loaded and/or unloaded. This step of measuring multiple uniformity waveforms for the same tire can often help improve the resolution of the estimation process. In one example, a uniformity parameter for a test tire may be measured while rotating in the clockwise direction (referred to herein as a direct measurement) and in the counterclockwise direction (referred to herein as an indirect measurement). This can be done by remounting the tire with barcode inside or barcode outside or by reversing the direction of rotation without a remounting.

In another example, different uniformity parameters may be measured in one or both directions for the same tire. For example, the radial run out of a tire (an unloaded tire parameter measurement) may be measured in one or both directions as well as the radial force variation (a loaded tire parameter measurement). Measurements of both a loaded tire and unloaded tire parameter can help account for any additional signal variations that may occur because of contact patch deformities being introduced to a tire during loading. Two loaded or two unloaded waveforms measured on a given test tire should embody the same process harmonic effect since the construction has not changed, only the measurement direction. However, to keep all obtained uniformity waveforms on the same measurement basis, it may be appropriate to apply a conversion to either the loaded or unloaded waveforms to account for the fact that run out is measured in millimeters while force variation is measured in kilograms of force ($kg_f$). Conversion between these two units can be implemented by applying a correction due to the spring rate of the particular tire being examined. This spring rate may be computed theoretically or empirically. In one example, a relationship between radial run out (RRO) and radial force variation (RFV) is that $$RRO \cong RFV + \left(25 \frac{kg_f}{mm}\right)$$

where RFV has units of $kg_f$ and the resulting units of RRO will be millimeters.

In still further examples, additional measurement passes of a uniformity waveform in the same directions (repeats) or at retesting can also be used to improve process harmonic identification. One advantage of this approach arises from the fact that four passes of each tire provides four times as many data points, e.g., 4*128=512. In the usual case, this many extra data points are expected to lead to a halving of all estimation error standard deviations. Similarly, differences taken between two waveforms can be used to estimate the measurement error directly which can help with the some estimation approaches.

A further advantage of using multiple passes of the same tire can arise from the fact that the actual measurement points may be different. For example, the trigger to begin the uniformity measurement may be the initial detection of the barcode. But since the barcode has some width this means that rotations in two directions may initiate measurements at slightly different points that are different by a barcode width. This means that one could be sampling 4*128=512 different points on the tire rather than simply having repeats of the same 128 points. This can improve the estimation's ability to separate closely related frequencies. One especially powerful method is to fit the process harmonic with the constraint that the direct/clockwise and indirect/counterclockwise results must be similar (even equal) when measuring force variation or similar loaded uniformity parameter, and to have such results be the same when measuring run out or similar unloaded uniformity parameter.

Referring still to FIG. 3, once the uniformity waveforms are conditioned in accordance with one or more of the disclosed improvements, the set of selected re-indexed uniformity waveforms is analyzed to determine magnitude and azimuth estimates for each candidate process harmonic for each test tire. In some embodiments, the analysis more particularly comprises steps 310, 312 and 314 as shown in FIG. 3. In step 310, the tire harmonics are subtracted out from the uniformity waveforms so that subsequent analysis can more particularly focus on the identification of process harmonics only. In step 312, the set of re-indexed uniformity waveforms is analyzed using regression analysis to solve for the rectangular coordinates corresponding to each candidate process harmonic for each test tire. In step 314, the rectangular coordinates are then used to determine magnitude and azimuth estimates for each process harmonic for each test tire.

Although the analysis described with reference to FIG. 3 may be conducted directly on the raw and/or conditioned uniformity data measured around the tire (i.e., conditioned by re-indexing and/or deleting selected data points around the joints), an additional optional step 310 may involve subtracting some of the tire harmonics from the conditioned uniformity waveform data. This may be done, for example, by applying Fourier decomposition or regression-based analysis to identify and then subtract out the contributions to the signal based on the tire harmonics. When regression-based analysis is employed, it should be appreciated that the selective removal of some tire harmonics may actually be implemented at the same time as step 312 when using regression techniques to solve for the process harmonic contributions. Although it is possible in theory to remove all the tire harmonics from the measured uniformity data, in practice it may be preferred to subtract out only a subset of the most influential tire harmonics so that there is more substance to the remaining signal for identification of process harmonics. In one exemplary embodiment, the first four harmonics ($1^{st}$, $2^{nd}$, $3^{rd}$, $4^{th}$) are subtracted out. In other exemplary embodiment, the first ten harmonics are subtracted out. It should be appreciated that any consecutive or non-consecutive subset of influential tire harmonics may be removed in accordance with optional step 310.

Referring still to FIG. 3, a next step 312 in the subject method involves constructing rectangular coordinate coefficients corresponding to the candidate process harmonic(s) for each test tire. These rectangular coordinate coefficients correspond to the sine and cosine terms that can be used to represent the contribution of each candidate process harmonic to each measured data point $U_n$ around a tire. For example, the contribution of the candidate process harmonics to each data point can be represented by the following equation:

$$U_n = \sum_{k=1}^{K} x_k \cos\left(2\pi h_k \cdot \frac{n}{N}\right) + y_k \sin\left(2\pi h_k \cdot \frac{n}{N}\right), \quad (1)$$

where K is the total number of candidate process harmonics that are selected for analysis and $h_k$ is the non-integer harmonic number for each of the $k^{th}$ candidate process harmonics. N is the length of the measured uniformity waveform, for n=1, 2, ..., N data points measured around a tire. The rectangular coordinates referred to for each $k^{th}$ process harmonic correspond to $(x_k, y_k)$. As such, the rectangular coordinate coefficients referred to in step 312 correspond to the respective cos $$\left(2\pi h_k \cdot \frac{n}{N}\right)$$

and $$\sin\left(2\pi h_k \cdot \frac{n}{N}\right)$$

terms for each process harmonic. As such, for K different candidate process harmonics, step 312 will involve calculating (K*N) cosine values and (K*N) sine values.

Referring still to FIG. 3, the next step 314 in the method is to use the rectangular coordinates to determine magnitude and azimuth estimates for each candidate process harmonic for each test tire. First, the rectangular coordinates $(x_k, y_k)$ for each $k^{th}$ process harmonic can be solved for using a regression-based analysis that regresses the uniformity waveform for a given test tire onto the sine and cosine terms (i.e., the rectangular coordinate coefficients) calculated in step 312. A linear regression-based signature analysis approach may use known data points to fit the equations set forth by equation (1) above. Once the rectangular coordinates $(x_k, y_k)$ are determined for each $k^{th}$ process harmonic for a given test tire, the magnitude ($MAG_k$) and azimuth ($AZIMUTH_k$) of each process harmonic is then determined in step 314 according to the following:

$$MAG_k = 2\sqrt{x_k^2 + y_k^2}. \tag{2a}$$

$$AZIMUTH_k = \arctan(y_k/x_k) \tag{2b}$$

It should be appreciated that steps 304-312 are performed for each tire in the set of test tires. This results in a magnitude estimate ($MAG_k$) and azimuth estimate ($AZIMUTH_k$) for each process harmonic k and each test tire l=1, 2, ..., L, where L is the total number of tires in the set of test tires.

Referring again to FIG. 3, once the different magnitudes for the process harmonic(s) are identified, it is possible to separate at least one of those process harmonics from the tire harmonics, leaving just the tire harmonics in a uniformity waveform. As such, step 316 in FIG. 3 involves optionally removing one or more selected process harmonics from the uniformity waveform. A next step 318 involves filtering the uniformity measurements to remove or reduce the effects of the candidate process harmonic(s). For example, given the estimate of a candidate process harmonic for each tire, it is possible to re-estimate the tire harmonics to make the measurements less affected by the data shifts caused by the process harmonics. In software implementation, the filtering step 318 can be performed separately from step 316 or as part of the extraction of the process harmonic from the tire harmonics. The extracted information (i.e., the process harmonic contribution) and/or the filtered tire harmonic information can then be provided as output to a user for subsequent analysis, including the provision of tire evaluation data via visual or graphical displays, the implementation of tire sorting to fit within certain customer performance limits, etc.

Figure 4:
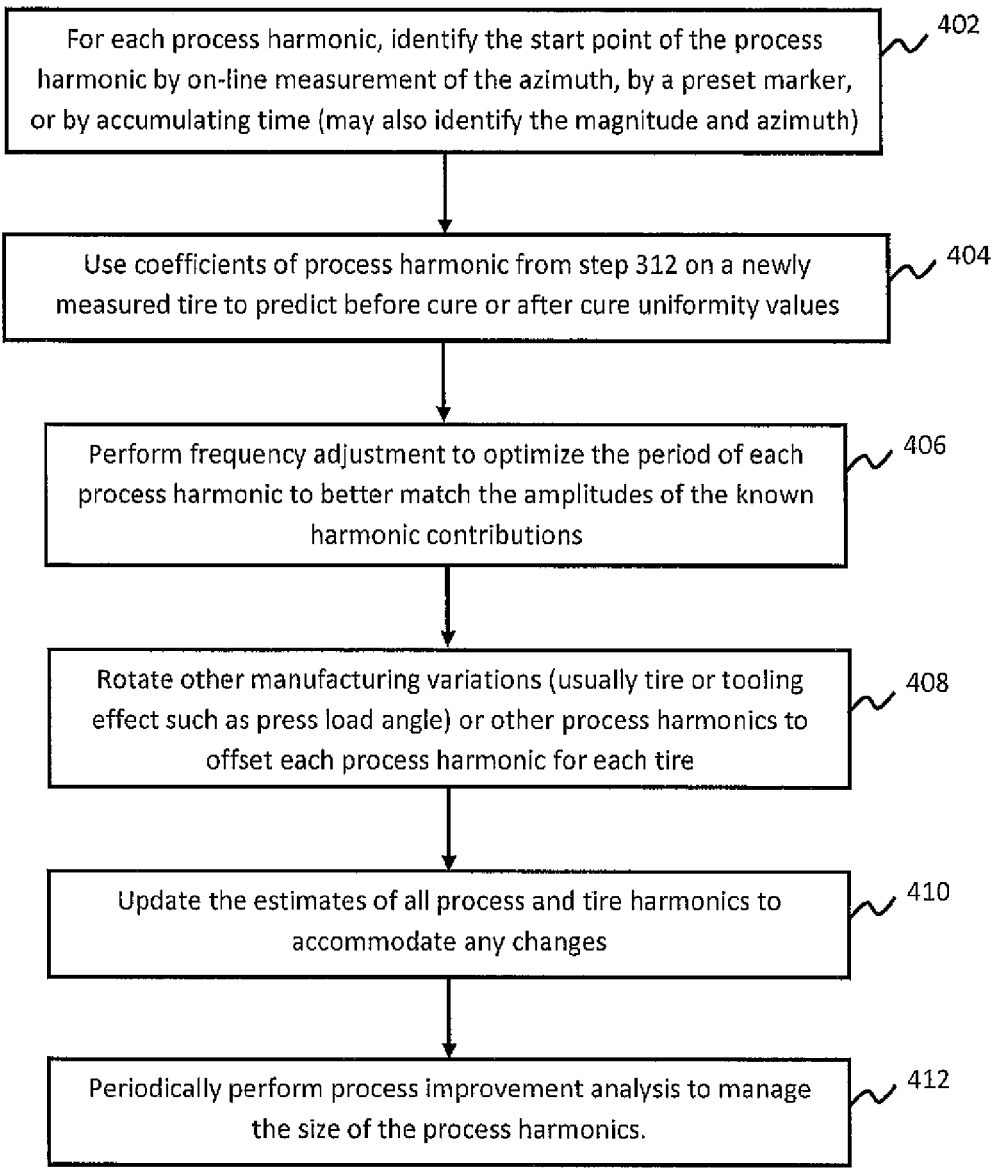
FIG. 4 provides a flow chart of exemplary steps in an improved method of improving tire manufacturing based on estimated process harmonics in accordance with the present technology.

FIG. 4 now shows a series of additional steps that may be selectively implemented in order to apply the improved method of estimating process harmonics to analyze other tires or to improve tires themselves. A first exemplary tire improvement step 402 involves identifying the start point of the process harmonic associated with a given manufacturing variation. In some embodiments, the relative location of a process harmonic can be determined with relation to a fixed element within a tire that is ultimately used for compensation, for example the location of a barcode.

A variety of different particular methods can be implemented in determining this relative relationship. In one example, the high point or other distinguishing feature of a process harmonic within a uniformity measurement (e.g., the maximum value in a radial run out measurement) can be measured directly in real-time using a laser, camera or the like. In another example, the location of a process harmonic element can be identified by using a reference mark such as a strip of tape or photocell using a camera, barcode reader, contact device or the like based on a previous measurement of this highpoint location. In a still further example, the location of a process harmonic can be computed by accumulating the number of cycles since some initial point. For instance, a 1.2 harmonic with peak at an azimuth of 0 degrees on tire 1 of a sequence will have its peak at an azimuth of 72 degrees on tire 2, at 144 degrees on tire 3, etc. In this case, the order of tire construction would have to be tracked.

Referring now to step 404, the coefficients of a process harmonic from step 312 along with the location knowledge from step 402 can be used to predict that process harmonic's contribution to the before cure or after cure uniformity values for a newly measured tire. In order to provide a prediction of the after cure uniformity value (such as the first harmonic of radial force variation), the known coefficients and location information for a given process harmonic can be combined with other known process effects (curing press, etc.) to provide the prediction. In order to provide a prediction of the before cure uniformity value (such as the first harmonic of the radial run out measured in a green tire carcass), the known coefficients and location information for a given process harmonic can be combined with other known process effects arising during the green construction of a tire, such as T-Rings, drums, etc.

Referring now to steps 406 and 408, both such exemplary steps are considered different ways to modify tire manufacture to change the relative location of the at least one candidate process harmonic within subsequent tires in order to reduce the combined average magnitude of the tire harmonics and the at least one candidate process harmonic. In step 406, an optional frequency adjustment step may involve optimizing the length of the period or the harmonic number of each process harmonic (such as tread thickness cycles) to better match the amplitudes of other known process harmonics (such as that resulting from a press). In one example, step 406 can be more particularly implemented by using the set of predicted after cure uniformity effects from step 404 to determine the change in process harmonic period that will provide a process harmonic amplitude more nearly equal to the after cure uniformity effects from the other known elements, and then make the change if desired. In another example, step 406 can be more particularly implemented by using the set of predicted before cure uniformity contributions from the step 404 to determine the change in process harmonic period that will provide a process harmonic amplitude more nearly equal to the before cure uniformity effects from the other known elements and then make the change as desired. This can be done in-line because the effect of changing the process harmonic period or harmonic number can be computed directly from Fourier methods.

Frequency adjustment step 406 may also be described as an adjustment to the manufacturing process of a tire in order to change the cyclic introduction of a process harmonic, thus directly altering the period or harmonic number associated with the process harmonic to better offset the set of identified tire and/or process harmonics in a tire. For example, a manufacturing process could be slowed or accelerated to introduce the process harmonic at a different location within a tire. In the example of a cyclic process effect introduced by variation in tread extruder thickness, it is possible to change the contribution of the process harmonic in a relatively simple fashion by changing the speed of the tread extruder thickness cycling. This could be done perhaps through a control system delay adjustment or by running the machine at a different cycle speed.

Figure 12:
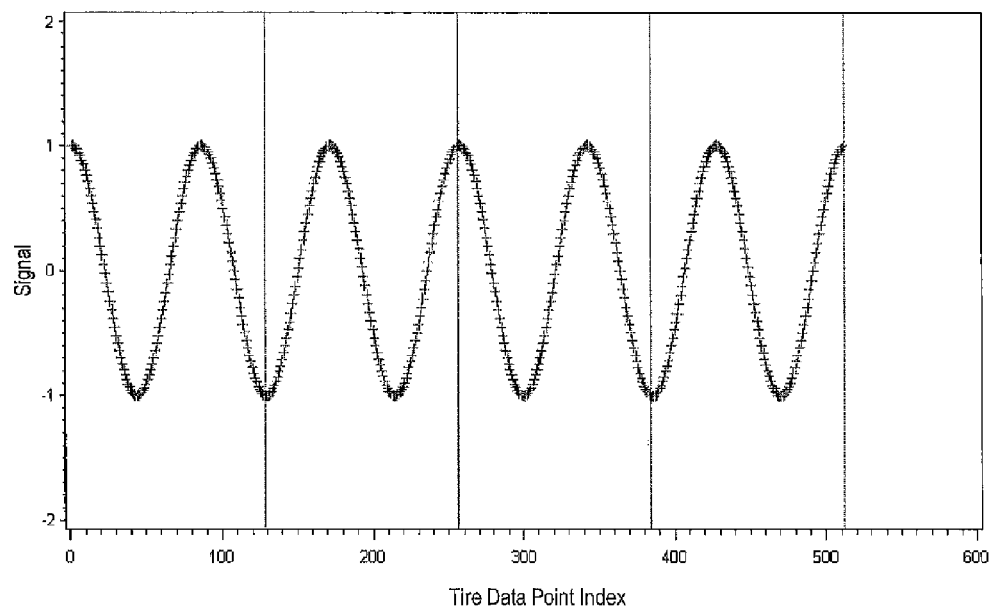
FIG. 12 provides a graphical illustration representing a particular process harmonic contribution to a tire, such as that introduced by a cyclic manufacturing variation in extruder thickness, where the process harmonic frequency is defined by a first exemplary cycle speed.
Figure 13:
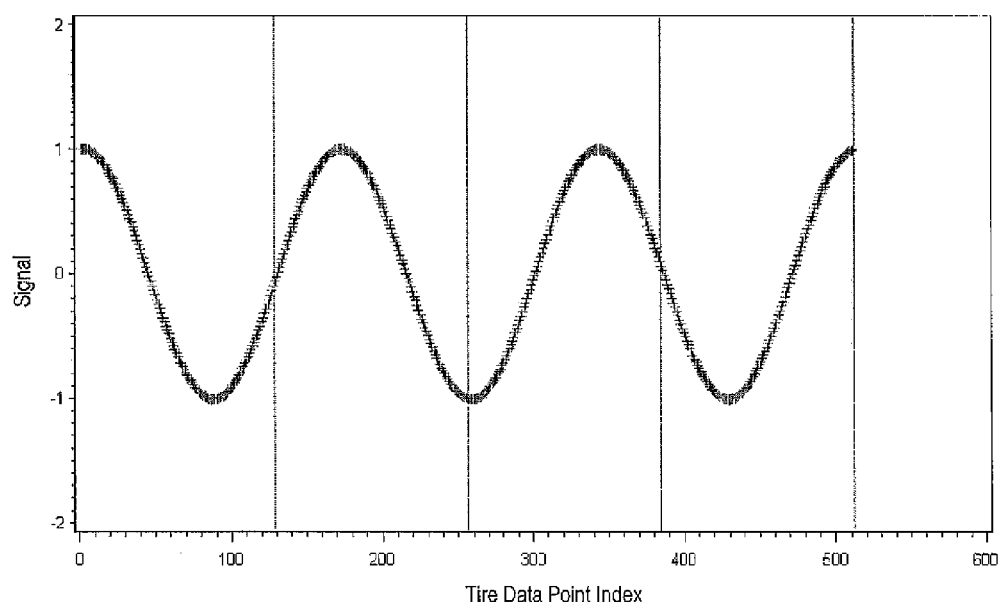
FIG. 13 provides a graphical illustration representing a particular process harmonic contribution to a tire such as represented in FIG. 12, where the process harmonic frequency is defined by a second exemplary cycle speed.

Providing a different process harmonic frequency (e.g., slowing down or speeding up the tread thickness extruder cycle) could provide a different amplitude for the harmonic components of each process harmonic. FIGS. 12 and 13 are intended to illustrate this phenomenon. FIGS. 12 and 13 respectively illustrate exemplary signals representing a process harmonic contribution caused by extruder thickness variation, with the process harmonic in FIG. 12 having a harmonic number of 1.5 and the process harmonic of FIG. 13 having a harmonic number of 0.75. The signal contribution in both FIGS. 12 and 13 is plotted relative to a tire data point index of 128 data points per tire for four consecutive tires as represented by the vertical lines in the graphs. Changing the tread extruder cycle speed from a first regular setting to a second slowed setting illustrates how this particular manufacturing variation affects the harmonic components of such process harmonic. For example, as can be better appreciated from the following table, changing the cycle speed causes a direct shift in the magnitudes of the first and second harmonic components (H1 and H2) of the process harmonic for the four consecutive tires. This shift in harmonic component contribution can be calculated as part of the subject methodology using Fourier analysis in order to determine the expected changes to the overall uniformity of a tire.

| Extruder setting | Tire | H1 mag | H2 mag |
|---|---|---|---|
| Regular | 1 | 0.53 | 0.73 |
| Slowed | 1 | 0.93 | 0.21 |
| Regular | 2 | 0.51 | 0.77 |
| Slowed | 2 | 0.89 | 0.19 |
| Regular | 3 | 0.55 | 0.70 |
| Slowed | 3 | 0.94 | 0.20 |
| Regular | 4 | 0.57 | 0.74 |
| Slowed | 4 | 0.90 | 0.17 |

Referring now to step 408, another potential improvement step corresponds to using the predicted uniformity value to choose an optimized relative placement of the process harmonic against other manufacturing variation contributions. In some examples, this might include rotating the location of a process harmonic resulting from a product support roller or a tooling effect such as a press load angle. The relative location of the other known uniformity contributions can be moved to compensate or adjust the frequency of the process harmonic in either the before cure or after cure representations. In after cure representations, an example of a known manufacturing variation to alter location is the curing press load angle. In before cure representations, an example of a known manufacturing variation to alter location is the unload angle of the transfer ring. Additional examples of before cure tire manipulation that may be used in some embodiments of the disclosed technology can be found in U.S. Pat. No. 6,856,929 and U.S. Patent Application Publication No. 2006/0231191, both of which are hereby incorporated by reference herein for all purposes.

Physical altering of various manufacturing steps or features may be implemented in order to achieve the manufacturing variation rotation and ultimate process harmonic offset desired as part of step 408. An improved manufacturing process implemented in accordance with step 408 or others ultimately reduces uniformity dispersion and increases customer yields (i.e., the number of tires having acceptable uniformity limits). In one example, an altered manufacturing step may involve altering the location of a process effect relative to other tire components (e.g., those creating the tire harmonics—joint overlap locations, press effects, etc.) so that the combined average magnitude of the tire and process effects (determined by vector algebra) is smaller or negligible, thus compensating for the existence of a process effect.

As part of step 408, another potential modification to the tire building process may involve altering the manufacturing variation itself that gives rise to a process harmonic to reduce or remove its effects. For example, the magnitude of an identified process harmonic can be reduced if its location cannot be controlled during production. Even when process harmonics are only reduced as opposed to removed, the cost of correcting tire uniformity will be reduced. For example, rectification procedures such as grinding the tread surface or adding extra material to the tire to improve tire uniformity will be implemented less often and in reduced quantities when required.

In a still further example, the manufacturing process can be adjusted to be robust to the anticipated and identified process harmonics. For example, uniformity dispersion might rise due to a periodic introduction of temperature variation. One could choose to fix the problem by installing an air-conditioning system in the manufacturing environment, but it might be more cost effective to reduce the impact of the variation by allowing the rubber time to relax. Since yield is often harmed more by instability and dispersion, this robust (to temperature) process could produce better yield than the perfect process which is never achieved. The robust process or design approach is often a quick, relatively easy way to improve processes without spending money or using resources.

Referring still to FIG. 4, an additional step 410 may involve periodically or automatically updating the estimates of all harmonic contributions to a uniformity waveform (including those that result in tire harmonics and process harmonics and including the sets of coefficients determined for each harmonic), to reflect any significant change in the process that might affect the performance of the subject system and method. In keeping with step 410, step 412 involves periodically performing process improvement analysis to manage the size of the process harmonics.

Figure 10:
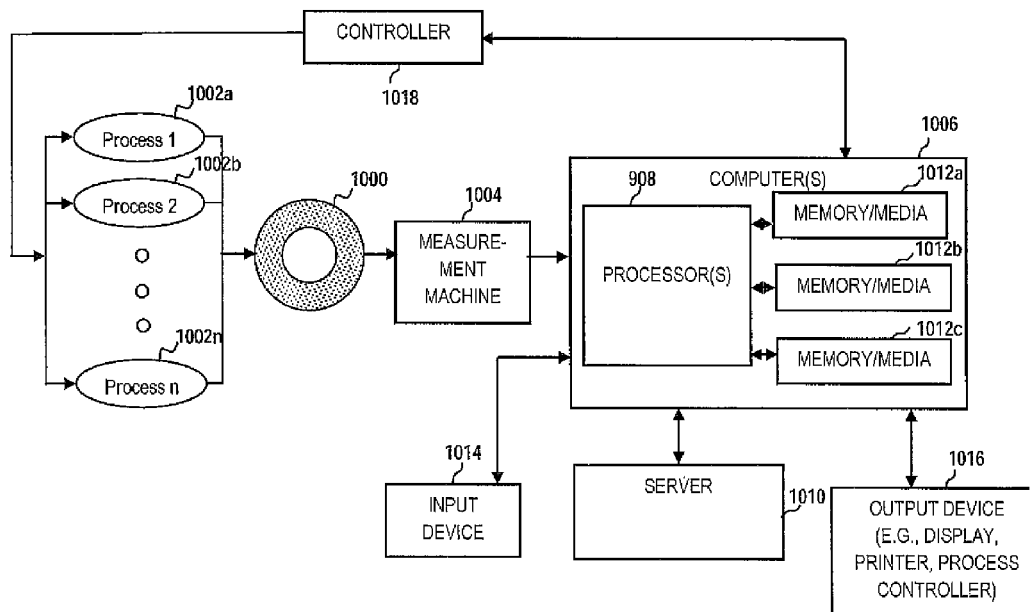
FIG. 10 provides a block diagram of exemplary hardware components for use in an embodiment of the disclosed system for improving tire uniformity.

Referring now to FIG. 10, a schematic overview of exemplary hardware components for implementing the above-described method is illustrated. An exemplary tire 1000 is constructed in accordance with a plurality of respective manufacturing processes. Such tire building processes may, for example, include applying various layers of rubber compound and/or other suitable materials to form the tire carcass, providing a tire belt portion and a tread portion to form the tire summit block, positioning a green tire in a curing press, and curing the finished green tire, etc. Such respective process elements are represented as 1002a, 1002*b*, . . . , 1002*n* in FIG. 10 and combine to form exemplary tire 1000. At least one of the process elements 1002 may introduce a manufacturing variation giving rise to a process harmonic that is identified for analysis in accordance with the subject methods. It should be appreciated that a batch of multiple tires may be constructed from one iteration of the various processes 1002*a* through 1002*n*. Often, it is such a batch of multiple tires that are measured and tested in accordance with the disclosed uniformity improvement techniques. The multiple model tires are then analyzed to improve the tire building process for subsequently manufactured tires.

Referring still to FIG. 10, a measurement machine 1004 is provided to obtain the various uniformity measurements obtained in step 304 of FIG. 3. In general, such a measurement machine may include such features as a mounting fixture on which a tire is mounted and rotated centrifugally at one or more predetermined speeds. In one example, laser sensors are employed to operate by contact, non-contact or near contact positioning relative to tire 1000 in order to determine the relative position of the tire surface at multiple data points (e.g., 128 points) as it rotates about a center line.

The measurements obtained by measurement machine 1004 may be relayed to one or more computers 1006, which may respectively contain one or more processors 1008, although only one computer and processor are shown in FIG. 10 for ease and clarity of illustration. Processor(s) 1008 may be configured to receive input data from input device 1014 or that is stored in memory 1012, including raw measurements of tire parameters. Processor(s) 1008, then analyze such measurements in accordance with the disclosed data conditioning and analysis, and provide useable output such as data to a user via output device 1016 or signals to a process controller 1018. Uniformity analysis may alternatively be implemented by one or more servers 1010 or across multiple computing and processing devices.

Various memory/media elements 1012*a*, 1012*b*, 1012*c* (collectively, "1012") may be provided as a single or multiple portions of one or more varieties of non-transitory computer-readable media, such as but not limited to any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others. The computing/processing devices of FIG. 10 may be adapted to function as a special-purpose machine providing desired functionality by accessing software instructions rendered in a computer-readable form stored in one or more of the memory/media elements. When software is used, any suitable programming, scripting, or other type of language or combinations of languages may be used to implement the teachings contained herein.

EXAMPLE 1

To better appreciate the techniques disclosed herein, particularly those represented in the flow charts of FIGS. 3 and 4, a numerical example of process harmonic based uniformity improvement is presented. This example illustrates how the disclosed techniques might be used in order to optimize the impacts of the manufacturing variations giving rise to process harmonics. Process harmonic optimization is an approach that seeks to oppose existing effects in order to balance them. Often, in practice, this means that one opposes a relatively uncontrolled process harmonic with a fixed harmonic from a tooling element such as a press. The optimization approach has the potential of making a tire better without requiring the simultaneous improvement of the components of the process. It can be used effectively to control the process with low cost while process improvement activities are being undertaken.

In accordance with such first example, step 302 involves identifying a candidate manufacturing variation and corresponding process harmonic such as that contributed by a tread cooling drum that has a 1 kg effect at 30 degrees measured relative to some point on its circumference. The harmonic number of such candidate process harmonic is also identified as 1.5 with respect to the tire line of interest. A set of uniformity waveforms for the process harmonic of interest is collected as described in step 304. Then all three improvements described in steps 304, 306 and 308 are implemented to obtain the re-indexed, partial, multiple direction data to remove joint effects and prepare the waveform data for the estimation of the known process harmonics.

Given this estimate of the cooling drum effect, one can then predict the impact of the effect on the final radial force first harmonic (RH1) simply by identify the starting point (or location of the peak) relative to each individual tire. One way to do this is to mark the high point of the drum with a piece of reflective tape that can be read with a photocell to determine its relative position to the barcode. One may also measure the out-of-round of the cooling drum in-line to accomplish this with the high point again being located relative to the barcode. Another option is to establish the position of the cooling drum high point (by intervention or measurement) at a single point t in a production sequence and then compute the number of cycles of the drum at any point greater than t. That is, knowing where the 1.5 process harmonic azimuth is for tire 1 in the sequence allows one to compute where its changed location will be for the nth tire in the sequence without subsequent measurement.

Figure 11:
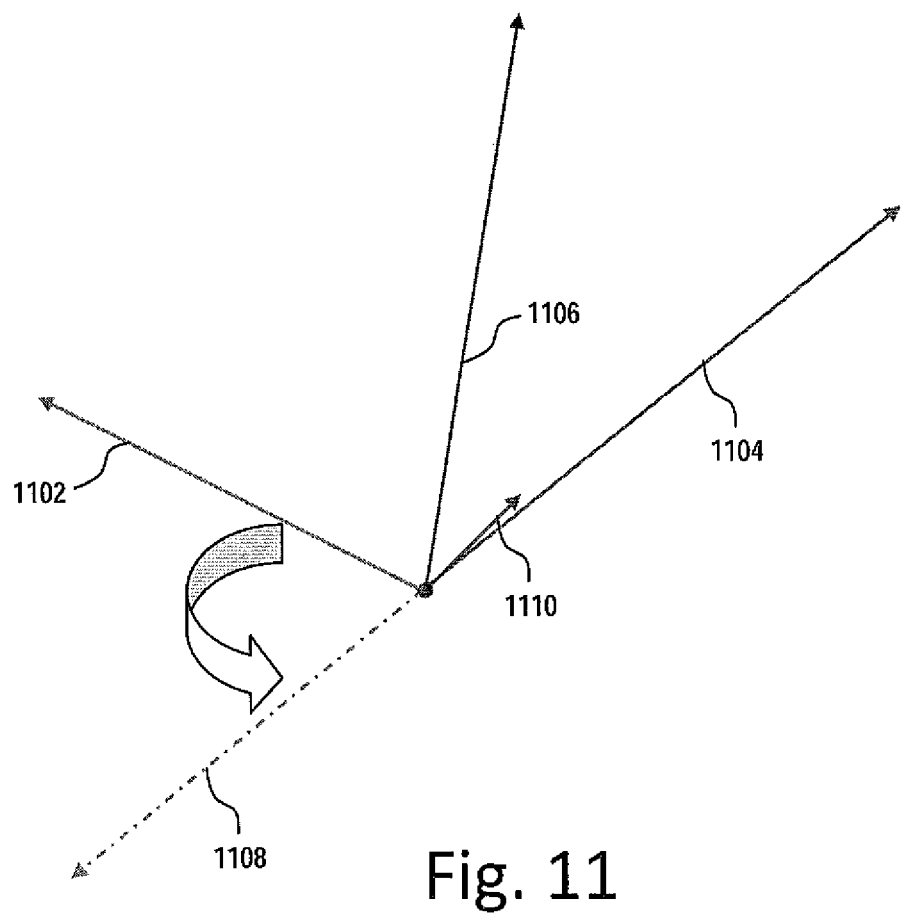
FIG. 11 provides a vector representation of potential uniformity improvements achieved by rotating process effects in accordance with the present technology.

Referring still to Example 1, this cooling drum RH1 effect is then one component of the RH1 effect which can be combined with other known effects (such as curing press) to predict the after cure RH1. Notice that when all building effects are constant (same drum, consistent joints, etc.) then this predicted RH1 high point will move entirely because of the cooling drum effect. One can then incrementally move the press load angle to place the press RH1 effect opposite the cooling drum effect to reduce the resultant RH1 value. This is depicted graphically in FIG. 11, where vector 1102 represents the initial cooling drum effect and vector 1104 represents the known press effect vector. The unoptimized resultant vector arising from the presence of vectors 1102 and 1104 is represented as vector 1106, which has a relatively high substantial magnitude. If, however, the disclosed techniques are used, the cooling drum effect vector can be rotated to an optimized location represented by vector 1108, such that when added with press effect vector 1104 a resultant optimized vector 1110 having a significantly less magnitude results.

Notice that this approach does not require measurement of a green tire vector directly but only knowledge of how it is expected to move. That is, one must only know the process harmonic characteristics, its harmonic number and amplitude, and its relative azimuth to the tire index to apply this method. One may use other fixed effects such as the transfer ring to compensate this tread cooling drum effect as well. Although the example is given in terms of the after cure RH1, this same approach can be applied to other after cure parameters and to before cure parameters such as FRH1 of a green tire to reduce the need for the measurement of cured parameters.

Since the process harmonic source will, in general, affect several harmonics (RH1, RH2, etc.) this process can be applied to each harmonic separately or to multiple harmonics simultaneously as needed. For a 1.5 process harmonic the entire set of resultant harmonics will be affected in a predictable pattern. This means that moving the relative azimuth of the tread cooling drum will affect the final resultant for all harmonics and especially for long period harmonics like H1-H5. If there is a corresponding press H1-H5, the rotation angle can be chosen to best balance all five effects.

An important additional advantage that is available when one does process harmonic adjustment is that the period of the effect can often be changed by slowing or speeding the process. For example if the 1.5 harmonic were the result of a poorly tuned extruder speed control system then one could change the period of this process harmonic by changing the response of the control system. A slower response should push the process harmonic down. For example, a slower response should shift the 1.5 harmonic (occurs 1.5 times every tire) to a 0.5 harmonic (occurs 0.5 times every tire). This shift can be directly computed from knowledge of Fourier methodology. A shift like this is not, in general, possible with fixed tooling elements unless they are adjustable in their diameters. An advanced system can choose the optimal speed for each process harmonic to optimize multiple tire harmonics with every tire, but it would also be possible to do this on a less frequent basis that would suffice for a stable process harmonic. For example, the baseline process harmonic RH1=1 kg and RH2=1 kg contributions at standard control system response time of $v_1$ might be shifted to 1.5 kg and 0.5 kg with a change of speed to $v_2$.

The potential advantages of using the disclosed process harmonic improvement methodology is limited only by the sizes of the inherent process effects and an ability to estimate them well. Based on current knowledge, it is expected that process harmonics account for nearly ⅔ of the RH1 dispersion with perhaps one-half of this (an absolute ½ of the full dispersion) available for process harmonic compensation purposes.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for improving the uniformity of tires in tire manufacture, comprising the steps of:
    identifying a candidate process harmonic and corresponding period for a set of consecutively produced test tires which each have a circumference, wherein the corresponding period of the candidate process harmonic, defined relative to the dimensions of the test tires, is not an integer divisor of the circumference;
    collecting a set of uniformity waveforms by measuring a uniformity waveform for each test tire, wherein each uniformity waveform contains one or more tire harmonics and the candidate process harmonic;
    re-indexing the collected uniformity waveforms so that breaks between the waveforms for the consecutive tires matches the physical order of the candidate process harmonic and combining the re-indexed waveforms into a concatenated waveform with a period corresponding to the period of the candidate process harmonic;
    analyzing the set of re-indexed uniformity waveforms to determine magnitude and azimuth estimates for the candidate process harmonic; and
    modifying the tire manufacture based on the magnitude and azimuth estimates for the candidate process harmonic by slowing or accelerating a manufacturing process to reduce the combined average magnitude of the one or more tire harmonics and the candidate process harmonic for subsequent tires created by the tire manufacture.

2. A method as in claim 1, further comprising deleting selected points from each waveform from the set of uniformity waveforms that represent joint effects or other non-sinusoidal process effects.

\* \* \* \* \*